(12) United States Patent
Kiernan et al.

(10) Patent No.: US 8,030,011 B2
(45) Date of Patent: Oct. 4, 2011

(54) BIOMARKERS AND ASSAYS FOR MYOCARDIAL INFARCTION

(75) Inventors: Urban A. Kiernan, Chandler, AZ (US); Dobrin Nedelkov, Tempe, AZ (US); Randall W. Nelson, Phoenix, AZ (US)

(73) Assignee: Intrinsic Bioprobes, Inc., Tempe, AZ (US)

( * ) Notice: Subject to any disclaimer, the term of this patent is extended or adjusted under 35 U.S.C. 154(b) by 0 days.

(21) Appl. No.: 12/906,885

(22) Filed: Oct. 18, 2010

(65) Prior Publication Data

US 2011/0124122 A1  May 26, 2011

Related U.S. Application Data

(60) Continuation of application No. 12/367,982, filed on Feb. 9, 2009, now Pat. No. 7,816,095, which is a division of application No. 11/343,625, filed on Jan. 30, 2006, now abandoned.

(60) Provisional application No. 60/593,614, filed on Jan. 28, 2005.

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 422/50; 530/300; 530/350

(58) Field of Classification Search ................ None
See application file for complete search history.

(56) References Cited

PUBLICATIONS

Patel et al. (Biochemical Journal, 1996, vol. 318, No. 3, pp. 1041-1049).
Bausserman et al. (Journal of Experimental Medicine, 1980, vol. 152, No. 3, pp. 641-656).

*Primary Examiner* — Lisa Cook
(74) *Attorney, Agent, or Firm* — Zeman-Mullen & Ford, LLP

(57) ABSTRACT

Presented herein are novel blood plasma/serum biomarkers related to cardiovascular disease. These newly identified biomarkers create the basis for multiple (single) assays using traditional bioassay technologies and when used in combination yield exceptional clinical sensitivity and specificity in the determination of myocardial infarction (MI). A multiplexed, mass spectrometric immunoassay (MSIA) able to simultaneously assay for the new/novel biomarkers as well other MI markers is also presented. Means and methods for evaluating data generated using multiple biomarkers in order to validate findings and further the use of the multiplexed MI assay in clinical, diagnostic and therapeutic uses is also included.

6 Claims, 6 Drawing Sheets

| Marker | Sensitivity | Specificity | PPV | NPV | Relative integral value determined for threshold | False Readings |
|---|---|---|---|---|---|---|
| SAA | 91.7 | 91.7 | 91.7 | 91.7 | 1.35 | FP = 4, FN = 4 |
| SSTTR | 95.8 | 97.9 | 97.8 | 95.9 | 0.45 | FP = 1, FN = 2 |
| MYO | 87.5 | 87.5 | 87.5 | 87.5 | 0.02 | FP = 6, FN = 6 |
| {S and T} | 87.5 | 89.6 | 89.4 | 87.7 | Same | FP = 5, FN = 6 |
| {S and M} | 79.2 | 79.2 | 79.2 | 79.2 | Same | FP = 10, FN = 10 |
| {T and M} | 83.3 | 85.4 | 85.1 | 83.6 | Same | FP = 7, FN = 8 |
| All three | 75.0 | 77.1 | 76.5 | 75.5 | Same | FP = 11, FN = 12 |
| {S and T} or {S and M} or {T and M} | 97.9 | 100 | 100 | 98.0 | Same | FP = 1, FN = 0 |

1. The sample set consisted of 48 MI-affected and 48 healthy individuals, with mean ages of 52 (range: 21- 66) and 51 (range: 21- 66), respectively.

FIG. 4

| Requirement (Marker above threshold) | Sens | Spec | PPV | NPV | Relative integral value used as reference level in classification | False Readings[2] |
|---|---|---|---|---|---|---|
| SAA | 89.5 | 80.5 | 53.1 | 96.8 | 1.35 | FP = 15, FN = 2 |
| SSTTR | 94.7 | 100 | 100 | 98.7 | 0.45 | FP = 0, FN = 1 |
| MYO | 89.5 | 81.8 | 54.8 | 96.9 | 0.02 | FP = 14, FN = 2 |
| {S and T} | 84.2 | 80.5 | 51.6 | 95.4 | Same | FP = 15, FN = 3 |
| {S and M} | 78.9 | 58.4 | 34.0 | 91.8 | Same | FP = 29, FN = 4 |
| {T and M} | 84.2 | 81.8 | 53.3 | 95.4 | Same | FP = 14, FN = 3 |
| All three | 73.7 | 58.4 | 32.6 | 90.0 | Same | FP = 29, FN = 5 |
| {S and T} or {S and M} or {T and M} | 100 | 97.5 | 89.5 | 100 | Same | FP = 2, FN = 0 |

2. The sample set consisted of 19 MI-affected and 77 healthy individuals, with mean ages of 52 (range: 21- 66) and 45 (range: 21- 69), respectively.

FIG. 5

| Requirement | Sensitivity | Specificity | PPV | NPV | Predicted Error[3] | False Readings |
|---|---|---|---|---|---|---|
| 3-Marker Multivariant | 100 | 98.7 | 95.0 | 100 | 1.83% | FP = 1, FN = 0 |

3. Error predicted from the 48/48 training set (3534 correct classifications for 3600 challenges).

FIG. 6

BIOMARKERS AND ASSAYS FOR MYOCARDIAL INFARCTION

CROSS-REFERENCE TO RELATED APPLICATIONS

This application is a continuation that claims priority to, and the benefit of, U.S. Ser. No. 12/367,982 filed Feb. 9, 2009, which application claims priority to, and the benefit of U.S. Ser. No. 11/343,625 filed Jan. 30, 2006, which application claims priority to, and the benefit of, U.S. Provisional Application No. 60/593,614, filed Jan. 28, 2005 which are hereby incorporated by reference in their entirety.

STATEMENT REGARDING FEDERALLY SPONSORED RESEARCH OR DEVELOPMENT

Financial assistance for this project was provided by the U.S. Government through the National Institutes of Health under Grant Numbers 5 R44 CA99117-03 and 5 R44 HL072671-03; and the United States Government may own certain rights to this invention.

FIELD OF INVENTION

The present invention relates to new and novel blood plasma/serum biomarkers, which yield exceptional clinical sensitivity and specificity in the determination of cardiovascular diseases, and particularly in the determination of myocardial infarction (MI). According to the present invention, these new biomarkers are discovered and identified in MI-affected individuals and validated in larger cohorts of individuals suffering from MI. The identification of the new biomarkers creates the basis for multiple (single) assays using traditional bioassay technologies. However, the present invention additionally provides for a multiplexed, mass spectrometric immunoassay (MSIA) that is able to simultaneously assay for the new/novel biomarkers as well other MI markers. Such cardiovascular biomarkers and their corresponding assays have significant application in the fields of: basic research and development, proteomics, protein structural characterization, drug discovery, drug-target discovery, therapeutic monitoring, clinical monitoring and diagnostics.

BACKGROUND OF THE INVENTION

Cardiovascular disease is the most frequent cause of death in the United States. Of the many cardiovascular diseases, myocardial infarction (MI) and stroke are identified as the most prominent in sudden onset syndromes, both requiring the need of immediate and urgent medical care. Critical to the rapid intervention of such cardiac events are point of care assays able to accurately determine the onset of a true event so that hospitalization and treatment are administered in an effective and economical manner. Regarding myocardial infarction (MI), such testing generally focuses on an established cardiac biomarker panel consisting of creatine kinase MB (CKMB), cardiac troponin (cTn) and myoglobin (MYO), as monitored from plasma/serum. Notably, these markers follow independent temporal curves, with each reaching its greatest clinical/diagnostic usefulness in time frames ranging from 2-to-24 hours post onset of chest pain. The generally reported predictive values of these biomarkers are CK-MB; sensitivity=99%, specificity=89%, Positive Predictive Value (PPV)=64%, Negative Predictive Value (NPV)=99.8%; Troponin I; sensitivity=33.3%, specificity=99.4%, PPV=78.6%, NPV=96.6%; MYO; sensitivity=84.6%, specificity=71.1%, PPV=20.4%, NPV=98.3%.

Of particular interest is the earliest responding marker, myoglobin, which may be used to establish negative predictive assessments—i.e., for ruling out MI—within ~3-hours of suspected onset. Used as a single marker with a reference level of >55-200 ng/mL (dependent upon the sex of the patient and the commercial assay in use), myoglobin is used to assess MI patients with reported PPV=20.4% and NPV=98.3%, (with clinical sensitivity and specificity of 84.6% and 71.1%, respectively) within 3 hours of admission into an emergency department. To improve the accuracy of prediction in MI candidates, myoglobin is often used in combination with either or both of the other established markers. Predictive values of PPV=19.0 and NPV=99.5 have been reported in studies using myoglobin in combination with one or both of CKMB and cTn in the same 3-hour time frame. These studies imply that the preferred means of MI determination is through multiple-marker assays employed at the earliest possible time after suspecting onset.

However, it is accurate to state that the predictive metrics of the conventional MI markers are far from perfect, regardless of whether used individually or in various combinations. Thus, there clearly exists a need for additional and improved high sensitivity and specificity tests able to rapidly differentiate between MI and complicating symptoms. Other than patient-in/patient-out determinations, these same tests are called upon as follow-through monitors able to gauge the effectiveness of treatment and detect the onset of secondary MI events. For these foregoing reasons, there is a pressing need to discover, identify and validate new biomarkers denoting the occurrence of MI as well as a need to improve the clinical sensitivity/specificity of existing cardiovascular biomarkers.

Described in this invention are new biomarkers found to be indicative of MI and the subsequent design of assays, including multiple-marker mass spectrometric immunoassays (MSIA), tailored for the determination of MI. Specifically, this invention describes newly discovered cardiovascular disease biomarkers; serum amyloid A and its variants (collectively referred to as SAA), and transthyretin and its variants (collectively referred to as TTR). As used herein, protein variants include but are not limited to, proteins having post-translational modifications or point mutations, proteolytic or chemical fragments of the protein, truncated forms of the protein, the protein in multimeric complexes, or any of the aforementioned in combination. Of particular importance are the SAA variant; intact wild-type SAA1$\alpha$ (SAA1$\alpha$) and the TTR variant sulfo-TTR (SS-TTR). Provisions are made to use these newly discovered cardiovascular biomarkers individually or in various combinations with themselves and/or other proteins for the accurate determination of MI. Also provided for is a multiplexed assay using variants of TTR, variants of SAA and variants of an existing MI biomarker, myoglobin (collectively referred to as MYO), to accurately determine MI.

Accordingly, this invention makes provisions for the concept of finding, identifying and using new biomarkers that are able to improve the clinical and diagnostic monitoring of cardiovascular diseases. Moreover, this invention makes provisions for designing and implementing assays able to analyze one or more markers found to be associated with MI. Finally, the present invention makes provisions for an analytical platform able to perform these assays in a multiplexed manner, and means of correlating the data (that include threshold detection and computer-assisted correlations) for improved clinical and diagnostic utility.

SUMMARY OF THE INVENTION

It is an objective of the present invention to provide for methods of discovering, identifying, validating and using biomarkers related to cardiovascular diseases including MI.

It is an object of the present invention to describe new biomarkers related to cardiovascular diseases including MI.

It is another object of the present invention to establish SAA and TTR (and their variants) as responsive to cardiovascular diseases including MI.

It is still another object of the present invention to use SAA or TTR (and their variants) in the determination, diagnosis and monitoring of cardiovascular diseases including MI.

It is yet another object of the present invention to measure the absolute or relative quantities or concentrations of SAA or TTR (and their variants) present in biofluids including blood, and use the measurement to determine, diagnose or monitor cardiovascular diseases including MI.

Another object of the present invention is to improve upon the predictive accuracy of existing MI markers for the determination, diagnosis and monitoring of MI by using data from the analysis of SAA or TTR (and their variants).

It is yet another object of the present invention to improve upon the accuracy of analyzing myoglobin for the determination, diagnosis and monitoring of MI by using data from the analysis of SAA or TTR (and their variants).

Another object of the present invention is to provide a multiplexed assay able to analyze for at least one of SAA or TTR (and their variants) in addition to other biomarkers significant to MI.

Yet another object of the present invention is to provide a multiplexed mass spectrometric immunoassay able to simultaneously analyze for various combinations of myoglobin, SAA and TTR (and their variants).

A further object of the invention is to use the measurement of the relative responses of SAA or TTR (and their variants) present in blood in combination with computer-assisted correlation in determining the presence of MI.

The present invention describes the discovery and identification of new biomarkers able to determine, diagnose and monitor for cardiovascular diseases including MI. Moreover, the present invention is shown to improve the accuracy of MI determination by monitoring signal responses of SAA or TTR (and their variants) as present in blood plasma or serum. This methodology is even further improved when data from the two new biomarkers are used in combination with a conventional MI marker, myoglobin. Furthermore, the present invention describes a preferred mass spectrometry-based assay able to simultaneously detect the selected biomarkers and data analysis methods that, when applied to the resulting data, result in the improved determination of MI. The novel features that are considered characteristic of the invention are set forth with particularity in the appended claims. The invention itself, however, both as to its structure and its operation together with the additional objects and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

FIG. 4 is a table showing relative integrals for SAA1a, SS-TTR and MYO that can be used as reference levels. The values were determined from using the 48/48 (MI/Healthy) sample set.

FIG. 5 is another table showing relative integrals for SAA1a, SS-TTR and MYO that can be used as reference levels. The values were determined from using the 19/77 (MI/Healthy) sample set.

FIG. 6 is a table showing the predicted error rate of the 48/48 (MI/Healthy) sample set using random forest classification of the 17/79 (MI/Healthy) sample set.

DETAILED DESCRIPTION

Figure 1:
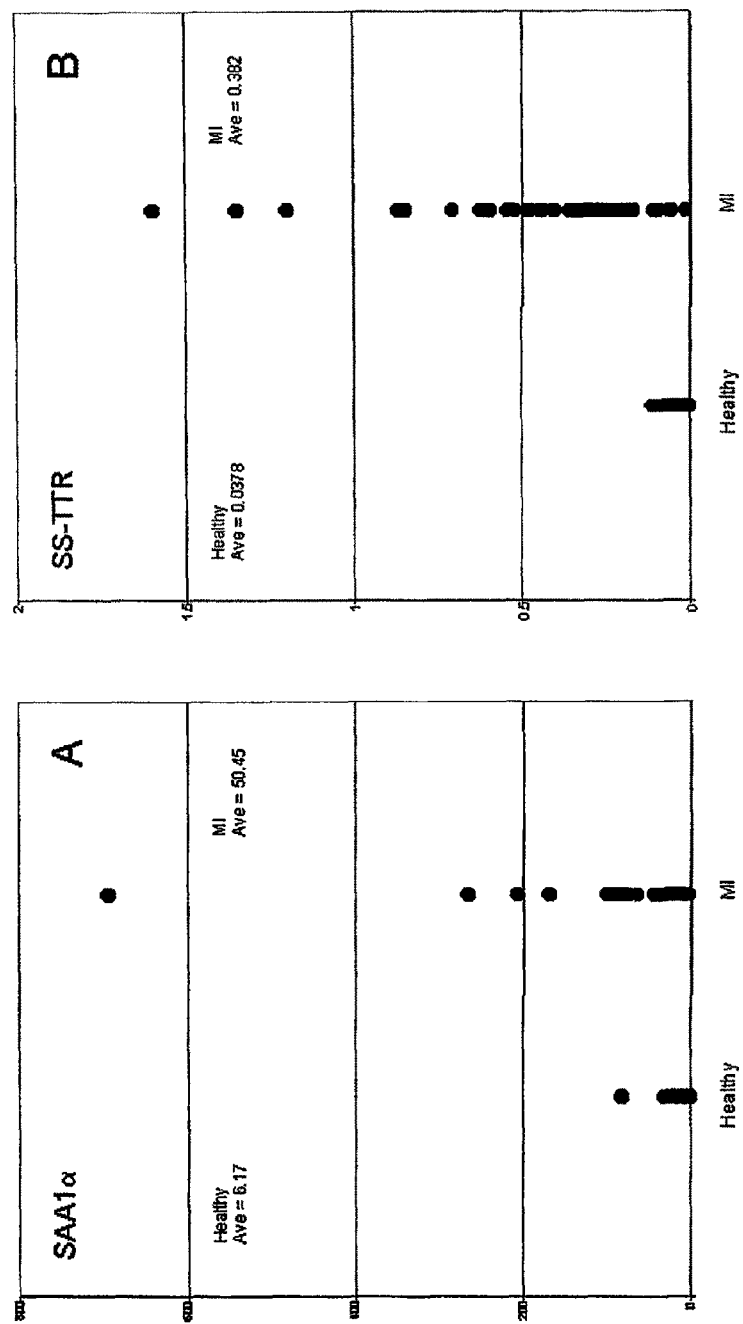
FIG. 1 shows relative integrals of SAA1α and SS-TTR for healthy and MI individuals. (A) The average value for SAA1α is observed to increase from 6.22 (s.d.=12.8; n=48)-to-50.5 (s.d.=108; n=48) for the healthy versus MI individuals, respectively. (B) The average value for SS-TTR is observed to increase from 0.038 (s.d.=0.026; n=48)-to-0.38 (s.d.=0.319; n=48) for the healthy versus MI individuals, respectively.

The present invention provides for methods that are able to discover, identify and validate biomarkers related to cardiovascular diseases including MI. In one exemplary embodiment, two new biomarkers, SAA having the sequence RSFF-SFLGEAFDGARDMWRAYSDMREANYIGSDKYFHAR GNYDAAKRGPGGVWAAE AISDARENIQRFFGH-GAEDSLADQAANEWGRSGKDPNHFRPAGLPEKY (SEQ ID NO: 1) and TTR having the sequence GPTGT-GESKCPLMVKVLDAVRGSPAINVAVHV-FRKAADDTWEPFASGKTSESGELHGL TTEEEFVEG-IYKVEIDTKSYWKALGISPFHEHAEVVFTANDSGPR RYTIAALLSPYSYST TAVVTNPKE (SEQ ID NO: 2) (and their variants), have been discovered to be responsive to cardiovascular diseases including MI. These new biomarkers are monitored individually, in combination with themselves, or in various combinations with existing biomarkers resulting in the determination, diagnosis and monitoring of cardiovascular diseases including MI. One or both of the newly discovered cardiac biomarkers may be monitored using a variety of analytical platforms including but not limited to, immunometric assays, ELISA, RIA, chromatography/electrophoretic assays, colorimetry, HPLC, CE, CZE, point-of-care assays, dip-stick based assays and in-home diagnostics, for the improved determination, diagnosis and monitoring of cardiovascular diseases including MI. In one exemplary embodiment, the markers can be monitored using independent assays and the results viewed collectively. In another exemplary embodiment, the multiple biomarkers are monitored simultaneously using a single analytical platform.

In an exemplary embodiment, both of the new biomarkers, (SAA, TTR and variants) are monitored using mass spectrometry methods able to detect, identify and quantify the species. This exemplary embodiment is expanded upon by including a known cardiovascular marker, myoglobin (MYO) into the assay. In another exemplary embodiment, variants of SAA, TTR and an existing biomarker (MYO) are selectively targeted from biofluids (e.g., blood, plasma, serum, urine, saliva) using selective isolation techniques prior to mass spectrometric analysis. A further exemplary embodiment is the use of multiplexed immunocapture methods able to selectively retrieve variants of SAA, TTR and an existing biomarker (e.g., MYO) prior to mass spectrometric analysis. In an additional exemplary embodiment, the qualitative and quantitative data resulting from the multiplexed mass spectrometric assays are used in the determination of MI by means of threshold detection or computer-assisted algorithms.

These and other embodiments of the present invention are now put forth by way of Examples meant to further clarify and illustrate the benefits of the invention.

Example 1

Preliminary Screening and Biomarker Identification

Previously, Nedelkov et al. reported on technologies and methodologies able to characterize full-length plasma proteins for the purpose of determining differences (e.g., identifying variants and quantitative modulations) found among the general population (PNAS 2005). In furthering this approach, we have developed 25 individual assays that have been incorporated into a high-throughput screening platform and used in creating a data foundation (in the healthy population) against which results from disease cohorts can be compared. The same panel of assays was applied to a small number of MI patients for the purpose of screening for putative markers. Essentially, MI samples were screened on a per protein basis to determine qualitative and/or quantitative differences away from foundational data. Noticeable qualitative (i.e., variants) and semi-quantitative differences were observed in two profiles resulting from the targeting of serum amyloid A (SAA) and transthyretin (TTR). The identities of the exact determinant species was established using mass mapping, chemical treatment and high performance mass spectrometry.

Serum amyloid A (SAA) describes a family of three genes found in humans (SAA1, SAA2 and SAA4), which produces proteins that act as apolipoproteins by chaperoning in the transport of high-density lipoprotein particles. During 'acute phase response'—the body's reaction to the immediate onset of inflammatory stimulus with the purpose of counteracting the challenges of tissue injury, infection and trauma—SAA1 and SAA2 levels in plasma have been shown to increase as much as 1000-fold from basal concentration of ~1-5 mg/L. Accordingly, low-levels of SAA can be used as a general indicator of good health, while higher levels may be a particularly useful indicator of chronic or immediate ailments. Important to the discussions at hand, we have previously noted a high degree of heterogeneity in SAA between individuals. There are at least three different causes of the microheterogeneity; simultaneous determination of both SAA1 and SAA2, variably truncated versions of the two major gene produces (generated post-translationally) and, point mutations contained in all forms of gene products. During a "verification" screen, the intact SAA1α species (104 amino acids; $M_r$=11,683) was found to be preferentially elevated in MI individuals versus the healthy controls (See FIG. 1A). Based on these observations, SAA1α was identified as a biomarker indicative of MI.

Transthyretin (TTR) is a non-covalently associated tetrameric protein, commonly found in serum and cerebral spinal fluid. Functionally, TTR serves unaccompanied in the transport of thyroid hormones or in complexes with other proteins in the transport of various biologically active compounds. Structurally, the wild-type (wt) TTR subunit is comprised of 127 amino acids and has a $M_r$ of 13,762. Previous studies suggest that TTR is able to undergo chemical modification induced by oxidative stress; however, oxidized variants of TTR have not previously been linked to cardiovascular diseases. During preliminary screening, a variant tentatively identified as S-sulfonated TTR (SS-TTR) was observed at high levels and at a notably high frequency relative to the control population. Subsequently, chemical reduction in conjunction with tryptic mass mapping and high performance mass spectrometry was used to confirm the site of S-sulfonation as Cys10. During the population-based screen, the SS-TTR variant was observed at elevated levels in the MI samples (See FIG. 1B). Given its high frequency of occurrence at elevated levels within the cardiac population, SS-TTR was identified as a biomarker indicative of MI.

Example 2

Biomarker Verification

Verification assays for SAA1α and SS-TTR were performed on 48 MI samples versus 48 healthy controls. SS-TTR assays were performed as described in Examples 3 and 4, with the exception of adding 30 µL of equine serum to each sample, containing equine SAA (eSAA; $M_r$=12,289), which was co-extracted and analyzed simultaneous to the human SAA in order to serve as an internal reference standard for relative quantification. Two data sets were produced, and ion signals from each set—sulfonated (SS)-TTR and cysteinylated (cys)-TTR, and, hSAA1α and eSAA—were baseline integrated over a mass range of 0.15% of the $M_r$ of each species using Proteome Analyzer Software (Intrinsic Bioprobes, Tempe, Ariz.). For comparison, the integrals for SS-TTR and hSAA1α were normalized to their respective internal references and the values plotted with respect to the health state of the individual. Results of this operation are shown in FIG. 1A and FIG. 1B, which illustrate elevated levels of SAA1a and SS-TTR present in individuals suffering from MI versus healthy population control.

Example 3

Multiplexed Mass Spectrometric Immunoassay

Based on the findings described above, a multiplexed MSIA was designed to target the two new putative biomarkers, SAA1α and SS-TTR, as well as the established MI marker myoglobin. Extraction devices for a multiplexed mass spectrometric immunoassay were prepared by coupling a mixture of mouse anti-human monoclonal antibody to serum amyloid A (MO-C40028A; Anogen, Mississauga, ON, Canada), rabbit anti-human polyclonal antibody to transthyretin (A0002; DakoCytomation, Carpinteria, Calif., USA) and goat anti-human polyclonal antibody to myoglobin (70-MG60; Fitzgerald, Concord, Mass., USA), to CDI (1,1'-Carbonyldiimidazole)-activated affinity-pipettes. Through side experiments, it was determined that a mixture of antibodies at the ratio of 0.08:0.04:0.10 mg/mL (SAA:TTR:MYO) was able to detect SAA and TTR at basal concentrations, and MYO at concentrations above 100 ng/mL. Using the extraction devices, each sample set was processed in parallel using a Beckman Multimek Automated 96-Channel Pipettor (Beckman Coulter, Fullerton, Calif., USA). The protein extraction/affinity capture process followed protocols where the multiplexed affinity pipettes were mounted onto the head of the Multimek pipettor and initially rinsed with 100 µL of HBS buffer (10 cycles, each cycle consisting of a single aspiration and dispense through the affinity pipette). Next, the pipettes were immersed into the sample tray and 150 aspirations and dispense cycles (100 µL volumes each) were performed, allowing for affinity capture of the targeted protein. Following affinity capture, the pipettes were rinsed with HBS (10 cycles), water (10 cycles), 2 M ammonium acetate-acetonitrile (4:1 v/v) mixture (10 cycles), and two final water rinses (10 cycles each). The affinity pipettes containing the retrieved protein were then rinsed with 10 mM N-octylglucoside (single cycle with a 150 µL aliquot) in order to homogenize the subsequent matrix draw and elution by completely wetting the porous affinity supports inside the pipettes. For elution of the captured proteins, MALDI matrix was prepared (α-cyano-4-hydroxycinnamic acid (6 g/L) in aqueous solution containing 33% (v/v) acetonitrile, 0.4% (v/v) trifluoroacetic acid), and 6 µL aliquots were aspired into each affinity pipette. After a 10 second delay (to allow for the dissociation of the protein from the capturing antibody, which is triggered by the low pH and chaotropic effects of the matrix), the eluates from all 96-affinity pipettes containing the targeted proteins were dispensed directly onto a 96-well formatted MALDI target. Samples were air-dried prior to mass analysis. MALDI-TOFMS was performed using a Bruker Autoflex MALDI-TOF mass spectrometer (Bruker Daltonics, Billerica, Mass.) operating in the linear mode. Mass spectra were the sum of five 50-laser shot spectra that were taken from different points within the spot area of each sample. Data were used with no further signal processing (i.e., smoothing or baseline leveling). Ion signals for SAA1α, SS-TTR, cys-TTR and MYO were integrated to baseline and normalized to the cys-TTR integral, resulting in a relative integral value for each target protein per individual. The values of these relative integrals were analyzed either manually or using Random Forest algorithm.

The resulting assay was able to detect SAA1α and TTR at basal (healthy) levels, however, it was only able detect myoglobin at levels above the clinical reference level (100±20 µg/L—as determined by side experiments). Thus, the assay automatically imposed a cut-off value for myoglobin equal to a physiological level commonly used for MI assessment with other analytical platforms thereby taking full advantage of past clinical findings relating myoglobin levels with myocardial infarction.

Example 4

Application Samples

Two sample sets were investigated in the course of study. The first set of 96-samples was comprised an equal number of healthy and MI-affected individuals (termed 48/48). The second study set of 96-samples was designed to more accurately reflect the natural occurrence of MI in the general population (19/77; MI/Healthy).

Heparinized human plasma samples (in 2-5 mL volumes) were obtained through ProMedDX (Norton, Mass., USA). Disease samples were collected from symptomatic individuals (42 male and 6 female, ages ranging from 21 to 66 years) who arrived at emergency rooms and were subsequently admitted and treated for MI. All diseased samples had elevated levels of CK-MB (Range: 32.0-319.1 µg/L). Information regarding the time of blood draw, e.g., time-from-onset (chest pain) or length of wait in the emergency room was unavailable. Age and sex matched healthy controls were also obtained for each sample set. The samples were collected at certified blood donor and medical centers, and provided labeled only with a barcode and an accompanying specification sheet containing information about the gender and age of each donor, thus ensuring proper privacy protection. All plasma samples were determined non-reactive for common blood infectious and were kept at −75° C. until use. Due to recent changes in HIPAA regulations, information regarding race was no longer available for all samples, and therefore not utilized in the sample selection criteria of this study.

Figure 2:
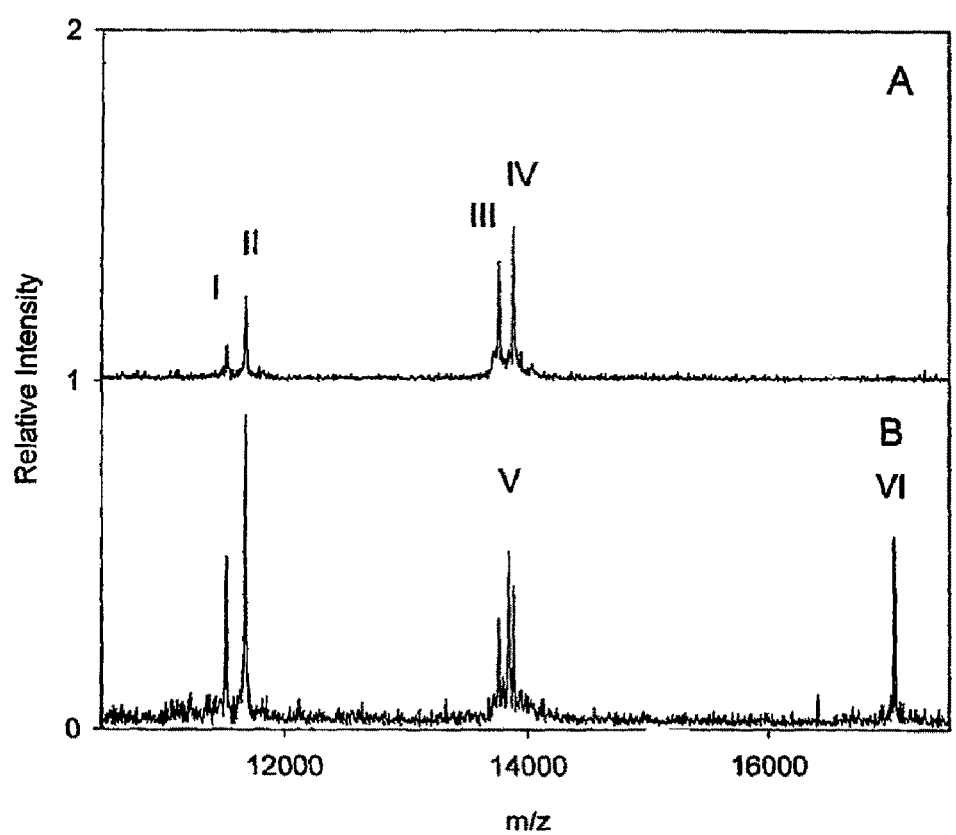
FIG. 2 illustrates spectra obtained from healthy and MI-affected samples. (A) A healthy individual where (I) des R-SAA1α, (II) SAA1α, (III) TTR and (IV) cys-TTR are observed. (B) An MI-affected individual where SAA1α, (V) SS-TTR and (VI) MYO are observed at elevated levels. Note that the spectra are normalized to cys-TTR, which was found present in all spectra and was thus used as an internal reference standard (i.e., relative integral=1.00). Relative integrals (of the markers) for all samples are shown in FIG. 3.
Figure 3:
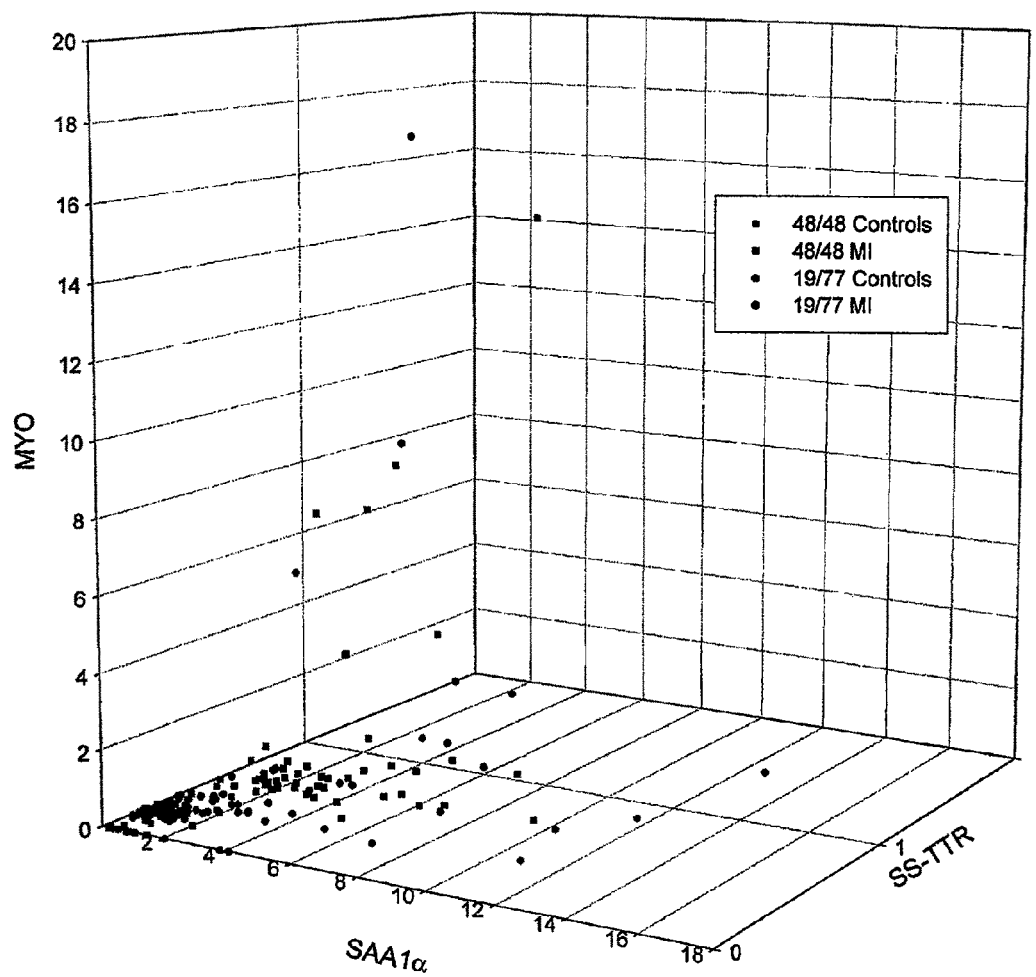
FIG. 3 depicts a three coordinate map plotting the relative integrals of SAA1α, SS-TTR and MYO. Values for controls (Red) and MI-affected (Blue) are given for both the 48/48 (Squares) and 19/77 (Circles) data sets.

Spectra resulting from the use of the tri-marker assay were found to differ both qualitatively and semi-quantitatively dependent on the individual under analysis. The extremes of these differences are shown in FIG. 2, which shows spectra obtained from a (A) healthy and (B) an MI-affected individual. FIG. 3 shows a three-coordinate map of the relative integrals of SAA1α, SS-TTR and MYO determined for the 192-samples under study. Notably, control samples from both sets (red circles and squares) are observed to cluster at relatively low values for two of the three markers, SS-TTR and MYO. Outliers from this cluster are observed predominantly for SAA1α values, however, clearly not to the degree observed for the MI samples (blue circles and squares).

Example 5

Data Evaluation Method 1—Independent Markers with Analytical Reference Levels

In the first data evaluation method, the 48/48 sample set was viewed as a training set in order to define relative integrals for each of the three markers that could be used as reference levels. In this process, each marker was treated individually to find an analytical reference level that equally balanced the number of false positives with the number of false negatives. This simple methodology was used to gauge the relative increase (if any) in predictive value that stems from the cooperative use of the three independent markers. FIG. 4 gives reference values determined from this exercise. Because of the original methodology—i.e., balancing the number of false readings when determining the threshold values, it is expected that all metrics will decrease when criteria require the presence of any one marker and another, or the presence of all three of the markers. Such is the case, as observed when the metrics for {SAA and TTR}, {SAA and MYO}, {TTR and MYO}, {SAA and TTR and MYO} are compared with their individual contributors. However, the predictive metrics are observed to increase when all combinations of two-marker assays are considered cooperatively—i.e., when {SAA and TTR}, or {SAA and MYO}, or {TTR and MYO} are used for classification. These results are viewed as encouraging in the use of the SAA/TTR/MYO tri-marker assay in the determination of MI and suggest the use of the cooperative two-marker approach in making MI classifications.

A second set of samples, proportioned 19/77 (MI/Healthy), was analyzed in order to challenge the tri-marker assay as applied to a general population that may require a point-of-care assay. All methodologies used in the 48/48 sample set remained the same with the exception of performing the analyses in a blinded and randomized manner. Only after analysis and classification were the true classifications of the sample revealed for correlation. FIG. 5 shows the results of the exercise. When the cooperative two-marker approach was used, only two of the 96 samples were incorrectly classified (as false positive), yielding results comparable to those of the training set.

Example 6

Data Evaluation Method 2—Random Forest Classification

Summarily, the results from different data evaluation methods (shown in Example 5) emphasize the use of multiple markers in cooperation to increase the predictive value of this assay. However, when using this evaluation method all of the markers were weighted equally—i.e., each yielded a yes/no answer based on whether it was above/below a threshold or reference level. As such, the evaluation method makes no provision for weighting the importance of each marker relative to MI, and accordingly may introduce minor biases into the results (i.e., give a marker slightly more of less credit than it deserves). We note here that data resulting from the multiplexed MSIA assay, which contains an imposed analytical limit of detection for myoglobin, ultimately requires more sophisticated multivariate approaches (able to weight variables) in order to eliminate such potential bias and reach the highest level of performance.

Data were subjected to a second evaluation using random forest classification applied to data shown in FIG. 3. Foremost, the 48/48 data set was evaluated for potential error rate. The data set was randomly split into a training set of 60 spectra and a challenge set of 36 spectra. The training data was used to build classification rules, from which the challenge data could be used to estimate error rates. In all, the procedure was repeated 100 times resulting in 3534 correct classifications for the 3600 challenges, which suggest an error rate of ~1.8%. Subsequently, the 48/48 data set was used as the training set with the 19/77 data set used as a challenge set (FIG. 6). A single false positive was observed, yielding a PPV and NPV of 95% and 100%, respectively. Notably, the new biomarkers and assay described in this research yielded predictive metrics that exceed those found using conventional MI biomarker assays.

The exemplary embodiments of the invention are described above in the Drawings and Description of Exemplary Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of the exemplary embodiments and best mode of the invention known to the applicant at the time of filing the application have been presented and are intended for the purposes of illustration and description. It is not intended to be exhaustive or to limit the invention to the precise form disclosed, and many modifications and variations are possible in the light of the above teachings. The exemplary embodiments were chosen and described in order to best explain the principles of the invention and its practical application and to enable others skilled in the art to best utilize the invention in various embodiments and with various modifications as are suited to the particular uses contemplated.

The invention claimed is:

1. A method for at least one of determining, diagnosing and monitoring a cardiovascular disease which includes the step of analyzing a biomarker which comprises at least one of serum amyloid a (SAA) and its variants.

2. The method of claim 1 wherein the biomarker comprises the SAA1α variant of SAA.

3. The method of claim 2 wherein the SAA1α variant of SAA is wild-type SAA1α.

4. The method of claim 2 wherein the SAA1α variant of SAA contains a point mutation.

5. The method of claim 2 wherein the SAA1α variant of SAA contains a posttranslational modification.

6. The method of claim 1 wherein the cardiovascular disease is myocardial infarction.

* * * * *

SEQUENCE LISTING

```
<160> NUMBER OF SEQ ID NOS: 2

<210> SEQ ID NO 1
<211> LENGTH: 104
<212> TYPE: PRT
<213> ORGANISM: Homo sapiens

<400> SEQUENCE: 1

Arg Ser Phe Phe Ser Phe Leu Gly Glu Ala Phe Asp Gly Ala Arg Asp
 1               5                  10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Val Trp Ala Ala Glu Ala Ile Ser Asp Ala Arg Glu Asn
    50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
```

```
                            85                  90                  95

Pro Ala Gly Leu Pro Glu Lys Tyr
            100

<210> SEQ ID NO 2
<211> LENGTH: 127
<212> TYPE: PRT
<213> ORGANISM: Homo sapiens

<400> SEQUENCE: 2

Gly Pro Thr Gly Thr Gly Glu Ser Lys Cys Pro Leu Met Val Lys Val
  1               5                  10                  15

Leu Asp Ala Val Arg Gly Ser Pro Ala Ile Asn Val Ala Val His Val
                 20                  25                  30

Phe Arg Lys Ala Ala Asp Asp Thr Trp Glu Pro Phe Ala Ser Gly Lys
             35                  40                  45

Thr Ser Glu Ser Gly Glu Leu His Gly Leu Thr Thr Glu Glu Glu Phe
         50                  55                  60

Val Glu Gly Ile Tyr Lys Val Glu Ile Asp Thr Lys Ser Tyr Trp Lys
 65                  70                  75                  80

Ala Leu Gly Ile Ser Pro Phe His Glu His Ala Glu Val Val Phe Thr
                 85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
            115                 120                 125
```